United States Patent [19]

Borsotti

[11] Patent Number: 4,628,123

[45] Date of Patent: Dec. 9, 1986

[54] PROCESS FOR THE SYNTHESIS OF 2-METHOXY-6-BROMO-NAPHTHALENE

[75] Inventor: Giampiero Borsotti, Novara, Italy

[73] Assignee: Montedison S.p.A., Milan, Italy

[21] Appl. No.: 790,220

[22] Filed: Oct. 22, 1985

[30] Foreign Application Priority Data

Oct. 23, 1984 [IT] Italy ............................. 23280 A/84

[51] Int. Cl.$^4$ ..................... C07C 41/22; C07C 41/24
[52] U.S. Cl. ................................................ 568/634
[58] Field of Search ........................................ 568/634

[56] References Cited

U.S. PATENT DOCUMENTS 4,137,272  1/1979  Papenfuhs et al. ............. 568/634 X

OTHER PUBLICATIONS

Hilgetag et al, Preparative Org. Chemistry (1972) 65–66.

*Primary Examiner*—Bernard Helfin

[57] ABSTRACT

A process for the synthesis of 2-methoxy-6-bromo-naphthalene, wherein the 2-methoxy-naphthalene is brominated by means of $Br_2$ to 1,6-dibromo-2-methoxy-naphthalene and the latter is then dehalogenated, without any separation from the liquid medium of reaction, by addition of iron.

12 Claims, No Drawings

PROCESS FOR THE SYNTHESIS OF 2-METHOXY-6-BROMO-NAPHTHALENE

The invention relates to a process for the synthesis of 2-methoxy-6-bromo-naphthalene, having the following formula:

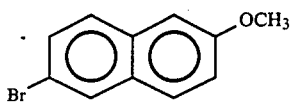

an intermediate in the preparation of an antiinflammatory product known by the trade mark "Naproxen" or "Naprosyn". The compound of formula (I) can be obtained by bromination of β-naphthol to 1,6-dibromo-β-naphthol, by dehalogenation of the latter to 6-bromo-β-naphthol by means of metallic tin and lastly by alkylation by means of dimethyl-sulphate or methanol, in the presence of acid catalysts. Tin, however, is a metal not very easily available, therefore the method proves to be of only slight interest from an industrial point of view.

A second, even more complicated, method is described in German patent No. 2.619.641. The process based on the dehalogenation by means of Sn, if it is applied to 1,6-dibromo-2-methoxynaphthalene, does not lead to high yields, because the methoxy group, under the reaction conditions, is hydrolyzed easily, resulting in the formation of remarkable amounts of the undesired product, 2-hydroxy-6-bromo-naphthalene.

Therefore an object of this invention is to provide a simpler process, that allows to obtain directly 2-methoxy-6-bromo-naphthalene with high yields, in only one reaction step, under extremely mild conditions and in a short time.

Now we have found that the above mentioned objects can be easily achieved by bromination of 2-methoxy-naphthalene, preferably in an acetic solution, or in a solution of another carboxylic acid, to 1,6-dibromo-2-methoxy-naphthalene and then by dehalogenation of the latter, without any separation from the liquid medium of reaction, by addition of metallic iron (for instance in the form of powder or chips).

The process can be represented schematically by the following equations:

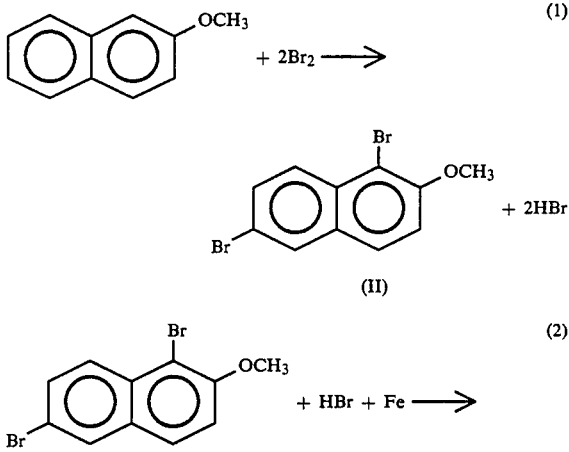

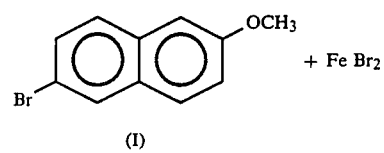

The combination:
"bromination + debromination"
in the presence of iron (that can be abbreviated to "bromo-debromo") can be applied to the simple naphthol as well.

The invention can be carried out in different ways; according to a preferred way, the process comprises the following steps, all of them carried out in only one apparatus and in only one medium:

(A) bromine, as such or diluted with $CH_3COOH$, is added under stirring, at 30°–50° C., to a solution of 2-methoxynaphthalene, trying carefully to keep in the liquid phase (during the addition and during the subsequent operations) the formed hydrobromic acid and adjusting, if necessary, the temperature by thermal exchange (indirectly by means of a refrigerant fluid, for instance water);

(B) the stirring is carried on always at temperatures ranging between 30° and 50° C., till 1,6-dibromo-2-methoxynaphthalene disappears;

(C) iron is added, in the form of powder or chips, keeping always the temperature, under stirring, between 30° and 60° C., provided the amount of hydrobromic acid, in the liquid medium of reaction, is at least equal to 2 moles per mole of dibromoderivative; the temperature can be higher than 60° C. as well, provided the liquid medium of reaction is always saturated with HBr;

(D) 2-methoxy-6-bromo-naphthalene is separated, after having diluted the reaction bulk, by filtration, decantation, centrifugation or extraction;

(E) 2-methoxy-6-bromo-naphthalene is purified by crystallization from suitable solvents, such as for instance aliphatic alcohols having from 1 to 4C atoms or aliphatic hydrocarbons such as cyclohexane, heptane, isooctane and so on.

Should iron be added in the form of powder, the amount of iron has to be substantially equal to at least 1 mole per mole of 2-methoxy-naphthalene fed at the start; in the case of iron in the form of chips, on the contrary, it is better to increase the lowest level to at least 3 moles/mole.

The process is surprisingly characterized in that only iron, among the most common and available metals, proves to be efficient for the above mentioned debromination. The use of similar, quite usual metals, such as Al, Mg and Zn, is quite ineffectual and leads only to the formation of hydrogen; by using iron, on the contrary, no hydrogen generation was noted, the dangerousness and undesirability of which is well known.

The following examples will illustrate the invention, without limiting, however, its scope.

EXAMPLE 1

A solution of 81 g of bromine in 25 cm³ of $CH_3COOH$ was added over 35 minutes to a very well stirred suspension of 39.25 g of 2-methoxy-naphthalene in 125 cm³ of glacial $CH_3COOH$, heated to 30° C., keeping the temperature at 40°–45° C., avoiding that the formed hydrobromic acid leaves the reaction medium; when the addition was over, the bulk was stirred for 1.5 h at 45° C. in order to complete the reaction. 14 g of iron in the form of powder were then added, in small doses, over 1.5 hours, slowing down at intervals the reaction exothermicity by means of a cold bath; one stirred at 45° C. till 1,6-dibromo-2-methoxy-naphthalene disappeared (on thin layer chromatography) and then the bulk was diluted with 0.5 liters of $H_2O$. Then the compound was filtered, washed with $H_2O$ and dissolved in $CH_2Cl_2$; lastly the chloromethylenic solution was washed with NaOH at 5%, dehydrated and evaporated. 55.2 g of raw 2-methoxy-6-bromo-naphthalene were obtained; after a crystallization from 250 $cm^3$ of isobutanol, 45 g of pure product were obtained (gas-chromatographic analysis) having a melting point ranging between 105° and 106° C.

EXAMPLE 2

Example 1 was repeated but omitting the dissolution in methylene chloride and thereby substantially obtaining (after crystallization from isobutanol) the same results.

EXAMPLE 3

Example 2 was repeated while replacing the iron powder with chips (of iron), thereby substantially obtaining the same results.

EXAMPLE 4

Example 2 was repeated while replacing the acetic acid with an equivalent amount of propionic acid, thereby substantially obtaining the same results.

EXAMPLE 5

Example 2 was repeated, while replacing the isobutanol with n-heptane, thereby obtaining excellent results.

What is claimed is:

1. A process for the synthesis of 2-methoxy-6-bromo-naphthalene, wherein 2-methoxy-naphthalene, in solution in a carboxylic acid, is brominated by means of bromine to 1,6-dibromo-2-methoxy-naphthalene and the latter is then dehalogenated, without any separation from the liquid medium of reaction, by the addition of iron.

2. A process according to claim 1, wherein iron is added in the form of powder, the iron amount being at least equal to 1 mole per mole of 2-methoxy-naphthalene fed at the start.

3. A process according to claim 1, wherein iron is added in the form of chips, the iron amount being at least equal to 3 moles per mole of 2-methoxy-naphthalene fed at the start.

4. A process according to claim 1, in which the carboxylic acid is acetic acid.

5. A process according to claim 4, wherein the temperature ranges between 30° and 60° C.

6. A process according to claim 4, wherein bromine is added in the form of acetic solution.

7. A process according to claim 4, wherein the amount of HBr, in the liquid medium of reaction, is at least equal to 2 moles per mole of dibromo derivative.

8. A process according to claim 4, wherein the pure 2-methoxy-6-bromo-naphthalene is recovered by distillation.

9. A process according to claim 4, in which the pure 2-methoxy-6-bromo-naphthalene is recovered by crystallization from a solvent thereof.

10. The process of claim 9, in which the solvent is an aliphatic alcohol.

11. The process of claim 9, in which the solvent is isobutanol.

12. The process of claim 9, in which the solvent is n-heptane.

* * * * *